United States Patent
Lyman

(10) Patent No.: US 10,012,622 B2
(45) Date of Patent: Jul. 3, 2018

(54) GASEOUS MERCURY DETECTION SYSTEMS, CALIBRATION SYSTEMS, AND RELATED METHODS

(71) Applicant: Seth N Lyman, Vernal, UT (US)

(72) Inventor: Seth N Lyman, Vernal, UT (US)

(73) Assignee: Utah State University, Logan, UT (US)

( * ) Notice: Subject to any disclaimer, the term of this patent is extended or adjusted under 35 U.S.C. 154(b) by 164 days.

(21) Appl. No.: 14/811,317

(22) Filed: Jul. 28, 2015

(65) Prior Publication Data
US 2016/0033456 A1 Feb. 4, 2016

Related U.S. Application Data

(60) Provisional application No. 62/030,517, filed on Jul. 29, 2014.

(51) Int. Cl.
*G01N 30/72* (2006.01)
*G01N 33/00* (2006.01)
(Continued)

(52) U.S. Cl.
CPC ......... *G01N 30/7206* (2013.01); *G01N 30/08* (2013.01); *G01N 33/0045* (2013.01);
(Continued)

(58) Field of Classification Search
CPC .............. G01N 30/08; G01N 30/7206; G01N 33/0045; G01N 2030/062;
(Continued)

(56) References Cited

U.S. PATENT DOCUMENTS 5,092,155 A * 3/1992 Rounbehler ............. G01N 1/02
436/156
6,131,440 A * 10/2000 Bertrand ................ G01N 30/30
73/23.35
(Continued)

OTHER PUBLICATIONS

Wieland, Thermal Decomposition of HgCl2 Vapour, Nature, vol. 156 p. 504-505 (1945).
(Continued)

*Primary Examiner* — Daniel S Larkin
*Assistant Examiner* — Nathaniel Kolb

(57) ABSTRACT

Embodiments disclosed herein are directed to gaseous mercury detection systems, calibration systems, and related methods. The gaseous mercury detection systems are configured to detect gas-phase mercury-compounds present in ambient air. For example, the gaseous mercury detection systems collect gas-phase mercury-compounds from ambient air and release the gas-phase mercury-compounds at concentrations capable of being measured by a gas-chromatography mass spectrometer without heating the gas-phase mercury-compounds above a decomposition temperature of at least one gaseous mercury compound that may present in the mercury-containing gas. The calibration systems are configured to determine an accuracy of or calibrate a gaseous mercury detection system. The disclosed calibration systems may be integrated with or distinct from the gaseous mercury detection systems disclosed herein.

8 Claims, 8 Drawing Sheets

(51) Int. Cl.
*H01J 49/04* (2006.01)
*G01N 30/08* (2006.01)
*G01N 30/62* (2006.01)
*G01N 30/02* (2006.01)
*G01N 30/12* (2006.01)
*G01N 30/14* (2006.01)

(52) U.S. Cl.
CPC .... *H01J 49/0422* (2013.01); *G01N 2030/025* (2013.01); *G01N 2030/085* (2013.01); *G01N 2030/121* (2013.01); *G01N 2030/143* (2013.01); *G01N 2030/626* (2013.01)

(58) Field of Classification Search
CPC ....... G01N 2030/143; G01N 2030/121; G01N 2030/122; H01J 49/0422
See application file for complete search history.

(56) References Cited

U.S. PATENT DOCUMENTS

| | | | | |
|---|---|---|---|---|
| 7,368,289 | B2 * | 5/2008 | Baldwin | G01N 1/2214 422/504 |
| 7,454,945 | B1 | 11/2008 | Kita et al. | |
| 2003/0200796 | A1 * | 10/2003 | Pawliszyn | G01N 30/00 73/64.47 |
| 2005/0061110 | A1 * | 3/2005 | Schaedlich | C22B 7/001 75/670 |
| 2010/0127217 | A1 * | 5/2010 | Lightowlers | G01N 21/359 252/373 |
| 2012/0205533 | A1 * | 8/2012 | Ariya | G01N 1/405 250/282 |
| 2015/0206726 | A1 * | 7/2015 | Ariya | G01N 1/405 250/281 |

OTHER PUBLICATIONS

U.S. National Library of Medicine Toxicology Data Network, Mercuric Oxide, retrieved from http://toxnet.nlm.nih.gov/ 22 Jul. 22, 2015.
Stern, Sulfates, High Temperature Properties and Thermal Decomposition of Inorganic Salts with Oxyanions p. 66 (2000).
Stern, Nitrites and Nitrates, High Temperature Properties and Thermal Decomposition of Inorganic Salts with Oxyanions p. 146-147 (2000).
Thorpe, Mercury, A Dictionary of Applied Chemistry vol. 3 p. 451-452 (1916).
Van Praagh, Electrochemistry, Physical Chemistry p. 267-268 (1950).
Brooks, Temperature and sunlight controls of mercury oxidation and deposition atop the Greenland ice sheet, Atmospheric Chemistry and Physics vol. 11 p. 8295-8306 (2011).
Jones et al., Detection and Quantification of gas-phase oxidized mercury compounds by GC/MS, Atmos. Meas. Tech., 9,2195-2205, May 18, 2016.
Lyman et al., Automated Calibration of Atmospheric Oxidized Mercury Measurements, Environ. Sc., Technol. 2016, 50, 12921-12927, Nov. 7, 2016.
E. Mendez-Lango et al., Triple point and melting point of mercury, 50th Calorimetry Conference 1995, Elsevier Science B.V., Mar. 19, 1996.

* cited by examiner

GASEOUS MERCURY DETECTION SYSTEMS, CALIBRATION SYSTEMS, AND RELATED METHODS

CROSS-REFERENCE TO RELATED APPLICATIONS

This application claims priority to U.S. Provisional Application No. 62/030,517 filed on 29 Jul. 2014, the disclosure of which is incorporated herein, in its entirety, by this reference.

GOVERNMENT SPONSORED RESEARCH

This invention was made with government support under government contract no. 1324781 awarded by the National Science Foundation. The government has certain rights in the invention.

BACKGROUND

Ambient air may contain Mercury (Hg), including gas-phase mercury-compounds. Gas-phase mercury compounds may include gaseous elemental mercury (GEM) or a gaseous mercury compound(s) (GMC), such as Mercury Bromide ($HgBr_2$), Mercury Chloride ($HgCl_2$), Mercury Oxide (HgO), Mercury Sulfate ($HgSO_4$), Mercury Nitrite ($Hg(NO_2)_2$), Mercury Nitrate ($Hg(NO_3)_2$), Mercury Iodide ($HgI_2$), or Mercury Fluoride ($HgF_2$). Other GMC types may also be present in ambient air.

About 1 $m^3$ to about 10 $m^3$ of ambient air may contain up to a few hundred picograms ($10^{-12}$ grams) of GEM or GMC. At these low concentrations, typical gaseous mercury detection systems, including gaseous mercury detection systems that include gas-chromatography mass spectrometers (GCMS), can be ineffective in accurately measuring GEM or GMC that may be present in ambient air.

Additionally, typical gaseous mercury detection systems do not measure GMC without decomposing through high-temperature treatment the GMC, i.e., the actual compounds, into their constituent components. Conventional GEM detection systems capture GEM or GMC from ambient air into a mercury collector and then release a high temperatures GEM or the elemental constituents of decomposed GMC into a detection device such as a cold vapor atomic fluorescence spectrometer. A conventional mercury detection system, however, does not measure a GMC as a compound, but as its constituent elements.

FIG. 1 is a schematic diagram of a prior-art GEM detection system 100. The GEM detection system 100 includes a mercury collector 102 (e.g., denuder) fluidly coupled to a mercury detector 104. Typically, ambient air flows through the mercury collector 102. The mercury collector 102 includes a collection surface 103 configured to capture GMC from the ambient air. The collection surface 103 may include a potassium chloride (KCl) coating. After collecting GMC, the mercury collector 104 and, in particular, the collection surface 103 is heated, using a heater 106, to a high temperature in an attempt to completely release or desorb all the GMC from the collection surface 103. Such a temperature may be in excess of about 500° C.

At those high temperature, e.g., temperatures around or above 500° C., most GMC will decompose into GEM and their elemental constituents. For example, a published decomposition temperature for Mercury Sulfate ($HgSO_4$) is 500° C. See Kurt H. Stern, High Temperature Properties and Thermal Decomposition of Inorganic Salts with Oxyanions, 21 Sep. 2000, p 66. Similarly, Mercury Nitrite ($Hg(NO_2)_2$) begins to decompose at a temperature as low as 50° C. and readily decomposes at 90° C. into Mercury Oxide (HgO) and Dinitrogen Trioxide ($N_2O_3$). See Id at 146. Mercury Nitrate ($Hg(NO_3)_2$) decomposes into Mercury Oxide (HgO) appreciably at 160° C. See Id at 147. Mercury Oxide (HgO) decomposes into GEM at under 400° C. G. See Van Praagh, Physical Chemistry, 1950, pp 267-268. Most GMC decomposes over a range of temperatures, but generally speaking, the higher the temperature, the faster the decomposition rate.

After heating the collection surface 103, the GEM or the elemental constituents of decomposed GMC released from the collection surface 103 then pass into the detector 104 to be measured. However, because the collection surface has been heated to temperatures in excess of the decomposition temperature of most GMC, the GMC will have decomposed into their elemental constituents, making the detector 104 unable to accurately detect concentrations of the GMC as compounds initially collected by the collection surface 103.

Accordingly, users and designers of gaseous mercury detection systems continue to seek improved detection systems.

SUMMARY

Embodiments disclosed herein are directed to gaseous mercury detection systems, calibration systems for use with any gaseous mercury detection system, and related methods. As will be discussed in more detail below, the gaseous mercury detection systems disclosed herein are configured to detect mercury-containing gases (e.g. gaseous elemental mercury (GEM) or gaseous mercury compounds (GMC or GMC) present in ambient air. For example, the gaseous mercury detection systems may collect GEM or GMC from ambient air and release the GEM or GMC at concentrations capable of being measured by a gas-chromatography mass spectrometers (GCMS) without heating the GMC above a decomposition temperature of at least one GMC that may have been collected. In another embodiment, the calibration systems disclosed herein are configured to determine an accuracy of and calibrate a gaseous mercury detection system including any of the gaseous mercury detection systems disclosed herein. The disclosed calibration systems may be integrated with or distinct from the gaseous mercury detection systems disclosed herein.

A gaseous mercury detection system is disclosed. The gaseous mercury detection system includes a mercury collection surface that is configured to cool the mercury collection surface to a temperature of about 5° C. above an ambient water dew point temperature and collect on the mercury collection surface at least one of gaseous elemental mercury (GEM) or a gaseous mercury compound (GMC) from a mercury-containing gas. The gaseous mercury detection system further includes a heater positioned and configured to heat the mercury collection surface to a first release temperature and release thereby the at least one of GEM or GMC collected. The first release temperature is below a decomposition temperature of the at least one GMC. The system further includes a sample trap fluidly coupled to the mercury collector. The sample trap is configured to capture the at least one of GEM or GMC released from the mercury collector at a temperature of about 0° C. or less and release the at least one of GEM or GMC captured in the sample trap at a second release temperature. The second release temperature is below the decomposition temperature of the at least one GMC. The system also includes a gas-chromatography mass spectrometer fluidly coupled to the sample trap to receive the at least one of GEM or GMC released from the sample trap. In embodiments, the first release temperature is between about 100° C. to about 300° C.

A gaseous mercury detection system may further include a calibration system. A calibration system includes a permeation oven configured to be heated to a selected temperature and fluidly coupled to the gas-chromatography mass spectrometer. The calibration system also includes one or more permeation tubes positioned within the permeation oven. Each of the one or more permeation tubes includes at least one of elemental mercury or a mercury compound and is configured to release the at least one of the elemental mercury or the mercury compound stored therein at the selected temperature as GEM or GMC.

In another embodiment, the permeation oven is fluidly coupled to the gas-chromatography mass spectrometer through the sample trap. A gaseous mercury detection system may further include a GEM detector fluidly coupled to the permeation oven and configured to detect the GEM. A valve may be fluidly coupled to the permeation oven. The valve may be configured to selectively control flow of the at least one of GEM or GMC released by the one or more permeation tubes to the gas-chromatography mass spectrometer or the GEM detector. Additionally, a pyrolyzer may be disposed between the GEM detector and the valve. The pyrolyzer may be configured to heat the at least one GMC to form GEM.

In embodiments, the gaseous mercury detection system may further include one or more conduits that fluidly couple the permeation oven with the gas-chromatography mass spectrometer. The one or more conduits may be heated to a temperature of about 100° C. to about 300° C. during operation.

A method of collecting and releasing gaseous elemental mercury (GEM) or a gaseous mercury compound (GMC) in ambient air is also disclosed. The method includes cooling a collection surface to a collection temperature of about an ambient water dew point temperature and drawing over the collection surface the ambient air at a collection flow rate. The method further includes collecting on the collection surface substantially all of the at least one of GEM or GMC present in the ambient air and heating the collection surface to a temperature sufficient to release the at least one of GEM or GMC therefrom and below a decomposition temperature of the at least one GMC. The method also includes releasing from the collection surface substantially all of the at least one of GEM or GMC collected thereon.

A method of measuring a quantity of GEM or GMC in ambient air is also disclosed. The measuring method includes collecting and releasing GEM or GMC in ambient air, as described above. The measuring method also includes cooling a sample trap to a temperature of about 0° C. or less and capturing the at least one of the GEM or GMC released from the mercury collector with a sample trap. The measuring method also includes heating the sample trap to a temperature greater than about 100° C. and below the decomposition temperature of the at least one GMC, desorbing the at least one of GEM or GMC from the sample trap. Finally, after heating the sample trap, the measurement method includes measuring at least one of a quantity of the GEM or GMC using a gas-chromatography mass spectrometer.

In embodiments, heating the collection surface in the measurement method includes heating the collection surface to a temperature of about 100° C. to about 300° C. In another embodiment, cooling the collection surface to a collection temperature includes cooling the collection surface to a collection temperature of five degrees above the ambient water dew point temperature. Similarly, in an embodiment, the collection flow rate may be between about 10 to about 100 liters per minute and collecting on the collection surface may occur over a period of 30 minutes to two hours. In another embodiment, cooling the sample trap includes cooling the sample trap to a temperature of about −50° C.

In another embodiment, the measurement method may include, prior to measuring, ionizing the at least one mercury-containing gas using an electron ionizer or a chemical ionizer.

The measurement method may further include calibrating the gas-chromatography mass spectrometer. The calibration method includes heating a permeation oven to a selected temperature, the permeation oven including one or more permeation tubes therein having at least one of elemental mercury or a mercury compound and configured to release the at least one of the elemental mercury or the mercury compound stored therein at the selected temperature as GEM or GMC. The calibration method further includes measuring the quantity of the at least one of the GEM or the GMC released by the one or more permeation tubes using the gas-chromatography mass spectrometer.

A calibration system is also disclosed. The calibration system includes a permeation oven configured to be heated to a selected temperature and one or more permeation tubes positioned within the permeation oven. Each of the one or more permeation tubes includes elemental mercury or a mercury compound and is configured to release the elemental mercury or the mercury compound stored therein at the selected temperature as GEM or GMC. The calibration system further includes a GEM detector configured to detect the GEM and one or more conduits coated with a substantially nonpolar coating and configured to fluidly couple the permeation oven to the GEM detector, the one or more conduits further configured to be heated to a temperature above about 120° C. during operation. In embodiments, the calibration system may further include a pyrolyzer configured to heat the at least one of GEM or at least one GMC to a temperature above the decomposition temperature of the GMC.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The foregoing features of embodiments of the present disclosure will become more fully apparent from the following description and appended claims, taken in conjunction with the accompanying drawings. Understanding that these drawings depict only typical embodiments of the present disclosure and are, therefore, not to be considered limiting of its scope, the embodiments of the present disclosure will be described with additional specificity and detail through use of the accompanying drawings in which:

DETAILED DESCRIPTION

Figure 1:
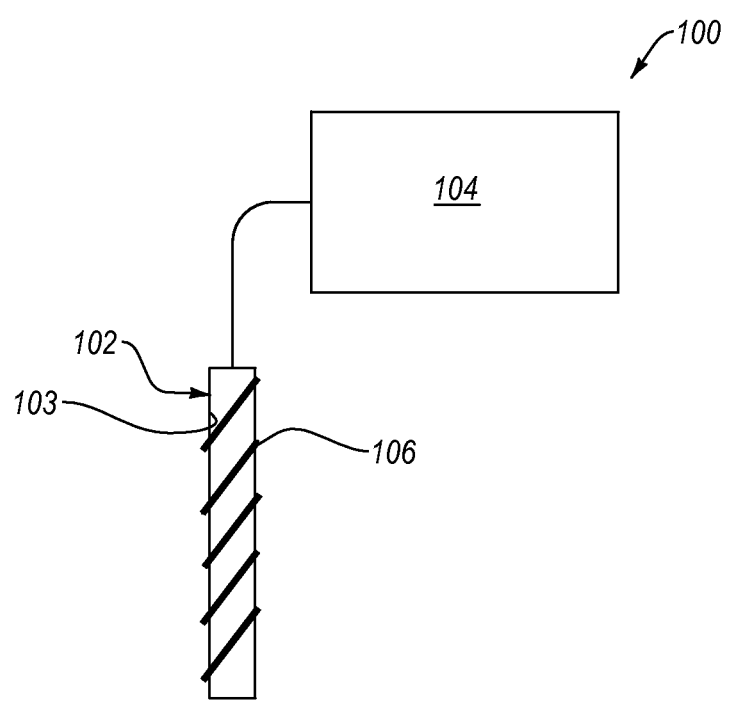
FIG. 1 is a schematic diagram of a prior-art GEM detection system.

Embodiments disclosed herein are directed to gaseous mercury detection systems, calibration systems for use with any gaseous mercury detection system, and related methods. As will be discussed in more detail below, the gaseous mercury detection systems disclosed herein are configured to detect gas-phase elemental mercury or gaseous mercury compounds (e.g. GEM or GMC) present in ambient air. For example, the gaseous mercury detection systems collect the low concentrations of GMC from ambient air and then release the GMC at a concentration capable of being measured by a GCMS without heating the GMC above a decomposition temperature of at least one GMC collected. The calibration systems disclosed herein are configured to determine the accuracy of and calibrate the gaseous mercury detection systems. The disclosed calibration systems may be integral with or distinct from the gaseous mercury detection systems.

In the following description, numerous specific details are provided for a thorough understanding of specific embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of additional embodiments. Thus, the following more detailed description of the embodiments, as illustrated in some aspects in the drawings, is not intended to limit the scope of the present disclosure, but is merely representative of the various embodiments of the present disclosure.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional", "optionally", or "or" refer, for example, to instances in which subsequently described circumstance may or may not occur, and include instances in which the circumstance occurs and instances in which the circumstance does not occur. The terms "one or more" and "at least one of . . . or . . . " refer, for example, to instances in which one of the subsequently described circumstances occurs, and to instances in which more than one of the subsequently described circumstances occurs.

Figure 2A:
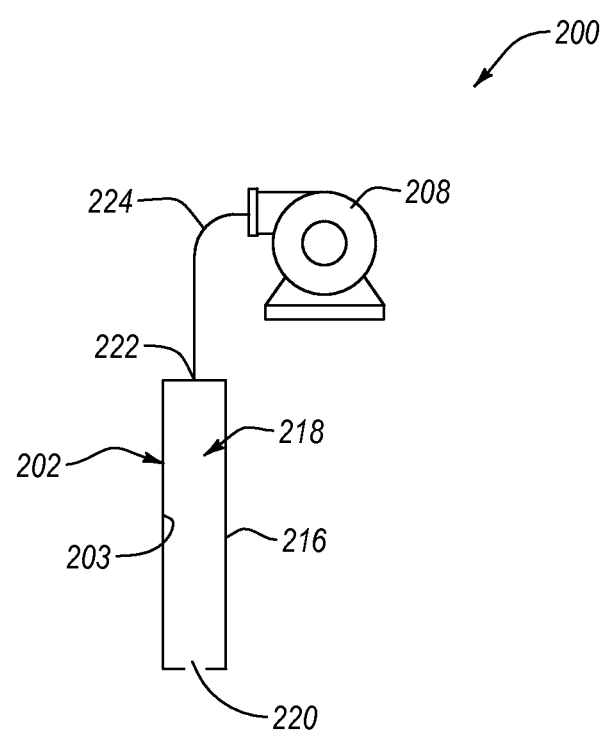
FIGS. 2A and 2B are schematic diagrams of different portions of a gaseous mercury detection system, according to an embodiment.
Figure 2B:
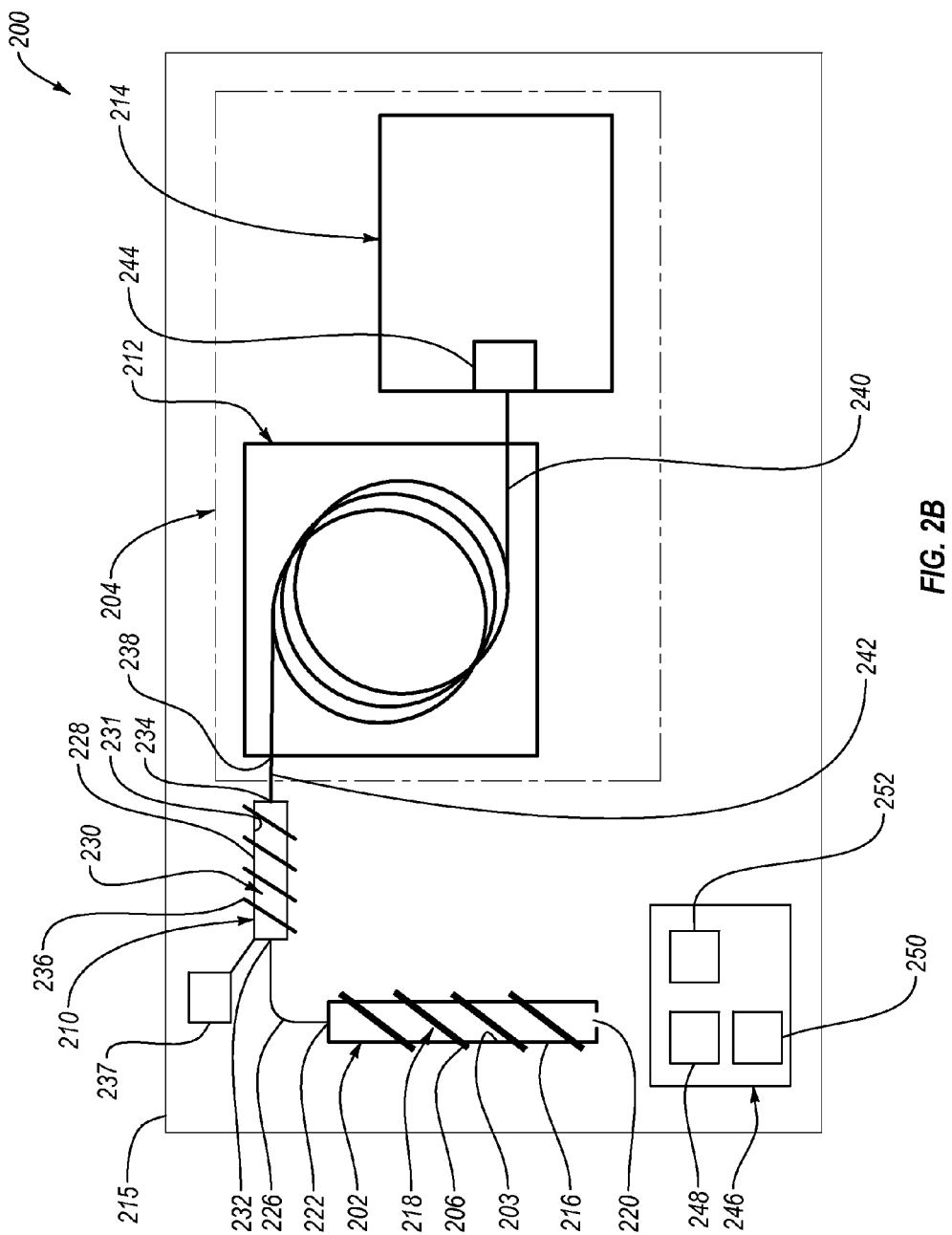

FIGS. 2A and 2B are schematic diagrams of different portions of a gaseous mercury detection system 200, according to an embodiment. The gaseous mercury detection system 200 may include a mercury collector 202 (e.g., a denuder) pneumatically coupled to a pump 208 (FIG. 2A). The pump 208 may be configured to draw and flow ambient air through the mercury collector 202. The mercury collector 202 includes a collection surface 203 configured to collect GMC from the ambient air flowing through the mercury collector 202. The mercury collector 202 is further configured to release GMC from the mercury collector 202 when heated to a first release temperature that is below a decomposition temperature of the at least one GMC that may have been collected on the mercury collector 202. The mercury collector 202 is further fluidly coupled to a sample trap 210 (e.g., a cryogenically cooled sample trap). The sample trap 210 includes a trapping surface 231 configured to be cooled to a temperature that captures the GEM or GMC thereon. The sample trap 210 and, in particular, the trapping surface 231, may be configured to release the GEM or GMC by heating the sample trap 210 and the trapping surface 231 thereof to a second release temperature that is below the decomposition temperature of the at least one GMC. In some embodiments, the sample trap 210 may be fluidly coupled to a GCMS 204. The sample trap 210 may be configured to release the GEM or GMC therefrom at a concentration that can be measured by the GCMS 204. The GCMS 204 may include a column 212 and a mass spectrometer 214. The GCMS 204 may be configured to detect at least one of GEM or GMC present in the at least one mercury-containing gas. In particular, the GCMS 204 may detect GMC because the gaseous mercury detection system 200 is not heated to a temperature above the decomposition temperature of the GMC. The gaseous mercury detection system 200 may further include a controller 246 that controls one or more components of the gaseous mercury detection system 200.

Referring to FIG. 2B, the gaseous mercury detection system 200 may be housed in a support structure 215. The mercury collector 202 may include a first wall 216 that partially defines an internal collection chamber 218. The first wall 216 may also include a first inlet 220 and a first outlet 222 spaced from the first outlet 222. The first inlet 220 and the first outlet 222 are in fluid communication such that ambient air can flow therebetween and through the collection chamber 218.

As discussed above, the mercury collector 202 includes the collection surface 203 that is at least partially positioned within or defines the collection chamber 218. The collection surface 203 may be positioned to be exposed to ambient air that flows through the collection chamber 218. In an embodiment, the collection surface 203 may be defined by a coating that coats at least a portion of the first wall 216. In an embodiment, the collection surface 203 may include a feature that is at least partially positioned within the collection chamber 218. For example, the feature may include a plurality of fibers, a plurality of beads, a grate-like structure extending from the wall 216, a generally foam-like structure, another suitable feature, or combinations thereof. At least a portion of the surface of the feature may form at least a portion of the collection surface 203. As such, the feature may increase a surface area of the collection surface 203 that is exposed to the ambient air flowing through the collection chamber 218. In some embodiments, increasing the surface area of the collection surface 203 may increase the quantity of GEM or GMC that is collected by the collection surface 203.

The collection surface 203 may include any surface or material configured to collect GEM or GMC from the ambient air flowing through the mercury collector 202. A GMC may be Mercury Bromide ($HgBr_2$ or $HgBr$), Mercury Chloride ($HgCl_2$), Mercury Oxide ($HgO$), Mercury Sulfate ($HgSO_4$), Mercury Nitrite ($Hg(NO_2)_2$), Mercury Nitrate ($Hg(NO_3)_2$), Mercury Iodide ($HgI_2$), Mercury Fluoride ($HgF_2$), or another GMC.

Additionally, in some embodiments, the collection surface 203 may be configured to collect and release GEM or GMC at one or more selected temperatures. For example, the collection surface 203 may include any surface or material that may collect GEM or GMC at ambient temperatures or below. For example, the mercury collector 202 may be configured to cool the collection surface 203 to a few degrees above an ambient water dew point temperature, e.g., five degrees above the ambient dew point temperature. Maintaining the collection surface 203 slightly above the ambient dew point temperature during the collection process allows the mercury collector 202 to capture GEM or GMC without also capturing significant amounts of water vapor in the ambient air. Condensed water vapor on the collection surface 203 could chemically interact with the GEM or GMC such that downstream measurements of GEM or GMC would be inaccurate.

Having a collection surface 203 that is maintained at or a few degrees above an ambient water dew point temperature may also negate the need to pre-condition or dry the ambient air prior to collecting GEM or GMC on the collection surface 203. Pre-conditioning, including filtering, or removing water vapor by cooling and then heating the ambient air, may cause some GMC to decompose on the conditioning surfaces. Thus, pre-conditioning the ambient air may lead to inaccurate quantification of GMC present in the ambient air.

Additionally, the collection surface 203 may include any surface or material configured to release the captured GEM or GMC at a first release temperature. The first release temperature or desorption temperature may be any temperature that is greater than the temperature at which the collection surface 203 collects the GEM or GMC and below a decomposition temperature of at least one (e.g., some or all) GMC collected by the collection surface 203. The release or desorption temperature for a given GMC is assumed to be below the range of decomposition temperatures of the same GMC. The decomposition temperature is a temperature at which the GMC begins to decompose into GEM and its elemental constituents. The published decomposition temperatures for various GMC is described in the background section. At least one GMC may partially decompose below the first release temperature due to factors unrelated to heat, such as barometric pressure, time, the presence of other chemical compounds, or the interaction of the GMC with the collection surface 203.

The time required to desorb GMS from the collection surface may vary depending on the type of collection surface, the GMC compound being desorbed, or other factors, but typical desorption times may be between 5 and 60 minutes.

The exact decomposition temperature may vary depending on which GMC are present. The inventor of the present disclosure has found that a release temperature of between 100° C. to about 200° C. provides a good desorption rate while preventing significant decomposition of most if not all GMC. As such, the first release temperature may be about 80° C. to about 300° C., such as 100° C. to about 200° C., about 140° C. to about 220° C., about 150° C. to about 200° C., or about 160° C. to about 180° C. However, in some embodiments, and for some GMC, the first release temperature may be greater than about 300° C.

The collection surface 203 may include any material that can collect GEM or a GMC at ambient temperatures or below and release the at least one mercury-containing gas at the first release temperature. In an embodiment, the collection surface 203 may include quartz (e.g., deactivated fused silica), nylon, polydimethylsiloxane (PDMS), another inert material, or combinations thereof. For example, the collection surface 203 may include a coating (e.g., a deactivated fused silica coating, a PDMS coating), a plurality of fibers (e.g., a plurality of quartz wool fibers, a plurality of PDMS-coated fibers, or combinations thereof), or combinations thereof.

In an embodiment, the first inlet 220 of the mercury collector 202 may be exposed to ambient air, while the first outlet 222 of the mercury collector 202 may be fluidly coupled to a pump 208 (FIG. 2A) via a first conduit 224. The pump 208 may be configured to draw and flow air through the first inlet 220 at a selected flow rate. A flow rate may be chosen to provide the correct air speed for the collection surface 203 to capture and retain substantially all of the GEM or GMC flowing over or through the collection surface 203. For example, the selected flow rate may be chosen to enable the collection surface 203 to collect GEM or GMC flowing thereover and retain the GEM or GMC previously collected by the collection surface 203.

Analogous to an air filter capturing and retaining particulate matter from an air stream, a high flow rate may provide more GEM or GMC flowing over or through the collection surface 203 but less GEM or GMC may be collected and retained on the collection surface 203 due to the high air velocities. Thus an excessively high flow rate could lead to inaccurate quantification of GEM or GMC present in the ambient air. Conversely, a low flow rate may provide for capturing substantially all of the GEM or GMC flowing over or through the collection surface 203 but an insufficient amount of GEM or GMC may be collected that might be later quantified by a GCMS, e.g., GCMS 204. A low flow rate may be compensated for by having a longer collection time. However, a longer collection time might also lead to an inaccurate quantification of GMC present in the ambient air as some GMC may decompose due to their interaction with the collection surface 203 over excessive time periods. Shorter collection times are preferred to prevent spontaneous decomposition of collected GMC over time. A low flow rate may also be compensated for by increasing the exposed area of collection surface 203. The rate at which the pump 208 draws ambient air through the first inlet 220 may be selected based on a volume of the collection chamber 218, an area of the first inlet 220 or the first outlet 222, a surface area of the collection surface 203 exposed to the ambient air, or a material from which the collection surface 203 is formed.

The inventor of the present disclosure has found a good collection rate and time is from between about 10 and 100 liters per minute (0.6 $m^3$ to about 6 $m^3$ per hour) over a period of 30 minutes to two hours. In other words, the pump 208 may draw ambient air through the first inlet 220 and over the collection surface 203 at that rate and for that duration to collect and derive an accurate quantification of GEM or GMC present in the ambient air. In some embodiments, e.g., with a larger collection surface 203, the pump 208 may be configured to draw air at a rate of more than 10 $m^3$/hr. The pump 208 may draw ambient air through the first inlet 220 in response to direction from the controller 246.

Referring to FIG. 2B, the mercury collector 202 may be thermally coupled to a first heater 206. The first heater 206 may be configured to heat the mercury collector 202 and, in particular, the collection surface 203 thereof, to a first release temperature. For example, the first heater 206 may include a resistive heating coil that is wrapped around an exterior of the mercury collector 202 or one or more Peltier cells thermally coupled to the mercury collector 202. In an embodiment, the first heater 206 may be at least partially positioned within, about, or incorporated into the mercury collector 202. The first heater 206 may also be configured to reduce the temperature of the mercury collector 202 to an ambient water dew point temperature or below (e.g., the first heater 206 may be integrated with cooling device to form a temperature control device that includes both heating and cooling elements). In particular, the first heater 206 may cool the mercury collector 202 from the first release temperature back to a few degrees within an ambient water dew point temperature. Similarly, the first heater 206 may maintain the mercury collector 202 at a selected temperature when the mercury collector 202 is in an environment that is above typical ambient temperatures. The first heater 206 may heat and cool (if integrated with a cooling device) the mercury collector 202 in response to direction from the controller 246.

A relatively low release temperature may cause the mercury collector 202 to release GEM or GMC at a concentration too low to be accurately measured by the GCMS 204. As such, embodiments of the gaseous mercury detection system 200 may further include a sample trap 210 that is fluidly coupled to the mercury collector 202 via one or more second conduits 226. The sample trap 210 may be configured to collect and then selectively release, by heating to different temperatures corresponding to different desorption temperatures of GEM or specific GMC types, GEM or GMC at a concentration that can be accurately measured by the GCMS 204.

In an embodiment, the mercury collector 202 may be fluidly coupled to both the pump 208 (FIG. 2A) and the sample trap 210 substantially simultaneously. Additionally or alternatively, the mercury collector 202 may be fluidly coupled to only one of the pump 208 or the sample trap 210 at a given time. For example, the mercury collector 202 may initially be fluidly coupled to the pump 208. After ambient air has flowed through the mercury collector 202, the mercury collector 202 may be fluidly decoupled (e.g., physically decoupled from) from the pump 208 and the mercury collector 202 may then be fluidly coupled to the sample trap 210. In this latter configuration, the mercury collector may be operated in the field and then returned to a laboratory environment to transfer the collected GEM or GMC to the sample trap 210.

In some embodiments, a carrier gas may be flowed from the mercury collector 202 to the sample trap 210 to facilitate the flow of GEM or GMC from the collection surface 203 to the sample trap 210. The carrier gas may include dry ambient air or, more particularly, a gas that is non-reactive with the at least one mercury-containing gas (e.g., Argon, Helium, or another noble gas or another inert gas). A dry, inert gas may increase the desorption rate or reduce or prevent the decomposition of GEM or GMC collected on the collection surface 203. A faster desorption rate or reduced decomposition of GEM or GMC will aid in more accurately measuring the quantity of GEM or GMC collected from the ambient air.

The sample trap 210 may include a second wall 228 that defines an internal trapping chamber 230. The trapping chamber 230 may further include a second inlet 232 and a second outlet 234 formed therein. The second outlet 234 may be spaced from the second inlet 232. The second inlet 232 may be fluidly coupled to the first outlet 222 through the second conduit 226. The sample trap 210 may further include a trapping surface 231 at least partially positioned within the trapping chamber 230. The trapping surface 231 may be attached to, at least partially positioned in, or incorporated into at least a portion of the second wall 228. In an embodiment, a portion of the trapping surface 231 may extend from the second wall 228 into trapping chamber 230. The trapping surface 231 may partially define the trapping chamber 230.

The trapping surface 231 may be cooled to a temperature sufficient to capture at least some of (e.g., substantially all of) the GEM or GMC flowing between the second inlet 232 and the second outlet 234. For example, the trapping surface 231 may be cooled to a condensation temperature of GEM or a GMC, typically in the range of 0° C. to as low as −50° C. The condensation temperature may be any temperature that causes at least one GEM or GMC captured in the mercury collector 202 to condense on the trapping surface 231. In an embodiment, the trapping surface 231 may be configured to capture a mercury-containing gas when the trapping surface 231 exhibits a temperature below about 0° C., such as below about −5° C., or below about −10° C.

In an embodiment, the trapping surface 231 may be cooled using a cooling device (not shown), including a chiller or a suitable cryogenic cooler that is thermally coupled to the trapping surface 231. In an embodiment, the sample trap 210 may include one or more Peltier cells for controlling the temperature of the sample trap 210. In an embodiment, the sample trap 210 may be cooled using any suitable cooling device known in the art.

In an embodiment, the sample trap 210 may further include a second heater 236 thermally coupled to the sample trap 210 and, in particular, the trapping surface 231. The second heater 236 may include a plurality of resistive heating coils wrapped around or incorporated into the sample trap 210, one or more Peltier cells, or any suitable heating device. The second heater 236 may be configured to rapidly heat the sample trap 210 and, in particular, the trapping surface 231 to a second release temperature. The second release temperature may include any temperature above the condensation temperature (e.g., greater than about 100° C.) and below a decomposition temperature of the at least one GMC that may be present in the at least one mercury-containing gas. For example, the second release temperature may about 100° C. to about 300° C., such as about 120° C. to about 250° C., and about 150° C. to about 200° C. In some embodiments, the second release temperature may be substantially similar to, greater than, or less than the first release temperature. The second heater 236 may be configured to rapidly heat the trapping surface 231 to the second release temperature in about 2 seconds to about 2 minutes, such as about 5 seconds to about 10 seconds, less than about 1 minute, or about 10 seconds to about 30 seconds. Rapidly heating the sample trap 210 may release the GEM or GMC in a concentration that may be accurately measured by the GCMS 204. In some embodiments, the cooling device may be integrated with the second heater 236 to form a temperature control device.

In an embodiment, the gaseous mercury detection system 200 may include a temperature control unit 237 communicably coupled to the sample trap 210. For example, the temperature control unit 237 may be incorporated into the sample trap 210, attached to the sample trap 210, may be remote from the sample trap 210, or may be incorporated into the controller 246. The temperature control unit 237 may direct the cooling device coupled to the sample trap 210 to cool the trapping surface 231 to the condensation temperature. Similarly, the temperature control unit 237 may be configured to direct the second heater 236 to rapidly heat the sample trap 210 to the second release temperature. In an embodiment, the temperature control unit 237 may be coupled to a thermometer (not shown) or other thermal sensor that determines the actual temperature of the sample trap 210. In some embodiments, the temperature control unit 237 may be omitted. In some embodiments, the temperature control unit 237 may be integrated with the controller 246.

In an embodiment, the temperature control unit 237 may also be communicably coupled to the mercury collector 202. In such an embodiment, the temperature control unit 237 may direct the first heater 206 to heat the mercury collector 202 to the release temperature. In an embodiment, the gaseous mercury detection system 200 may be communicably coupled to a separate temperature control unit. Alternatively, the mercury collector 202 may not be communicably coupled to a temperature control unit.

The column 212 of the GCMS may include one or more column inlets 238 and one or more column outlets 240 that are spaced from the column inlet 238. The column 212 may be fluidly coupled to the sample trap 210. For example, the second outlet 234 of the sample trap 210 may be fluidly coupled to the column inlet 238 via one or more third conduits 242. In some embodiments, a carrier gas may be flowed from the sample trap 210 to the GCMS 204 to help flow the at least one mercury-containing gas from the sample trap 210 to the column 212. The carrier gas may include ambient air or, more particularly, a gas that is non-reactive with the at least one mercury-containing gas (e.g., Argon, Helium, or other noble gas and/or other inert gas). The carrier gas may also be easily chemically distinguishable by the GCMS 204 from the at least one mercury-containing gas to be analyzed.

The column 212 may include a stationary phase (not shown) therein. The stationary phase may be positioned within the column 212 such that a mobile phase (e.g., the GEM or GMC) flows through at least a portion of the stationary phase. The stationary phase may include a substantially nonpolar stationary phase. For example, the stationary phase may include deactivated fused silica or PDMS. The substantially nonpolar stationary phase may be less likely to have GEM or GMC strongly adhere thereto.

The mass spectrometer 214 of the GCMS 204 may be fluidly coupled to the column outlet 240 of the column 212. Upon entering the mass spectrometer 214, the GEM or GMC may be ionized using an ionizer 244. In an embodiment, the ionizer 244 may include an electron ionizer. The electron ionizer may bombard the GEM or GMC with free electrons that are emitted from a filament to ionize the GEM or GMC. The GEM or GMC may or may not be cooled before being ionized. In an embodiment, the ionizer 244 may include a chemical ionizer. The chemical ionizer may be less likely to fragment or decompose any GMC present into its individual elements than the electron ionizer. The chemical ionizer may introduce a reagent gas, such as methane. The reagent gas then chemically interacts with the GEM or GMC to ionize the GEM or GMC. The ionizer 244 may ionize the GEM or GMC in response to direction from the controller 246.

After the GEM or GMC is ionized, the mass spectrometer 214 may analyze the GEM or GMC to determine a quantity of GEM or GMC present. The mass spectrometer 214 used to analyze the GEM or GMC may include a mass selective detector, an ion trap mass spectrometer, a magnetic sector mass spectrometer, or another suitable mass spectrometer. The mass spectrometer 214 may measure the GEM or GMC in response to direction from the controller 246.

In some embodiments, one or more components of the gaseous mercury detection system 200 may be heated to a temperature below the decomposition temperature of at least one GMC present to at least partially prevent (e.g., substantially prevent) the GMC from sticking thereto. For example, at least one of the second conduit 226, the third conduit 242, the column 212, or another component of the gaseous mercury detection system 200 may be heated to about 100° C. to about 300° C., such as about 150° C. to about 250° C. In such a case, the gaseous mercury detection system 200 may include one or more heaters (not shown) that heats the one or more components. Additionally, the temperature of the one or more components of the gaseous mercury detection system 200 may be controlled by the temperature control unit 237, by another temperature control unit, or by the controller 246. In an embodiment, one or more components of the gaseous mercury detection system 200 may include a substantially nonpolar coating that coats an interior surface thereof that contacts the GEM or GMC. The coating may at least partially prevent (e.g., substantially prevent) the GEM or GMC from sticking thereto. For example, at least one of the second conduit 226, the third conduit 242, the column 212, or another component of the gaseous mercury detection system 200 may include deactivated fused silica material/coating or PDMS coating applied to an internal surface thereof.

As previously discussed, the controller 246 may be configured to control one or more components of the gaseous mercury detection system 200. The controller 246 may include a user interface 248 configured to enable a user of the gaseous mercury detection system 200 to communicate with the controller 246. For example, the user interface 248 may enable a user to upload instructions into the gaseous mercury detection system 200. Additionally, the user interface 248 may enable the controller 246 to communicate information to the user, such as the status of an operation or the quantities of GEM or GMC detected by the GCMS 204. The controller 246 may further include memory 250 configured to store instructions and programs thereon. The controller 246 may further include one or more processors 252 configured to execute the instructions and programs stored on the memory 250.

Figure 3:
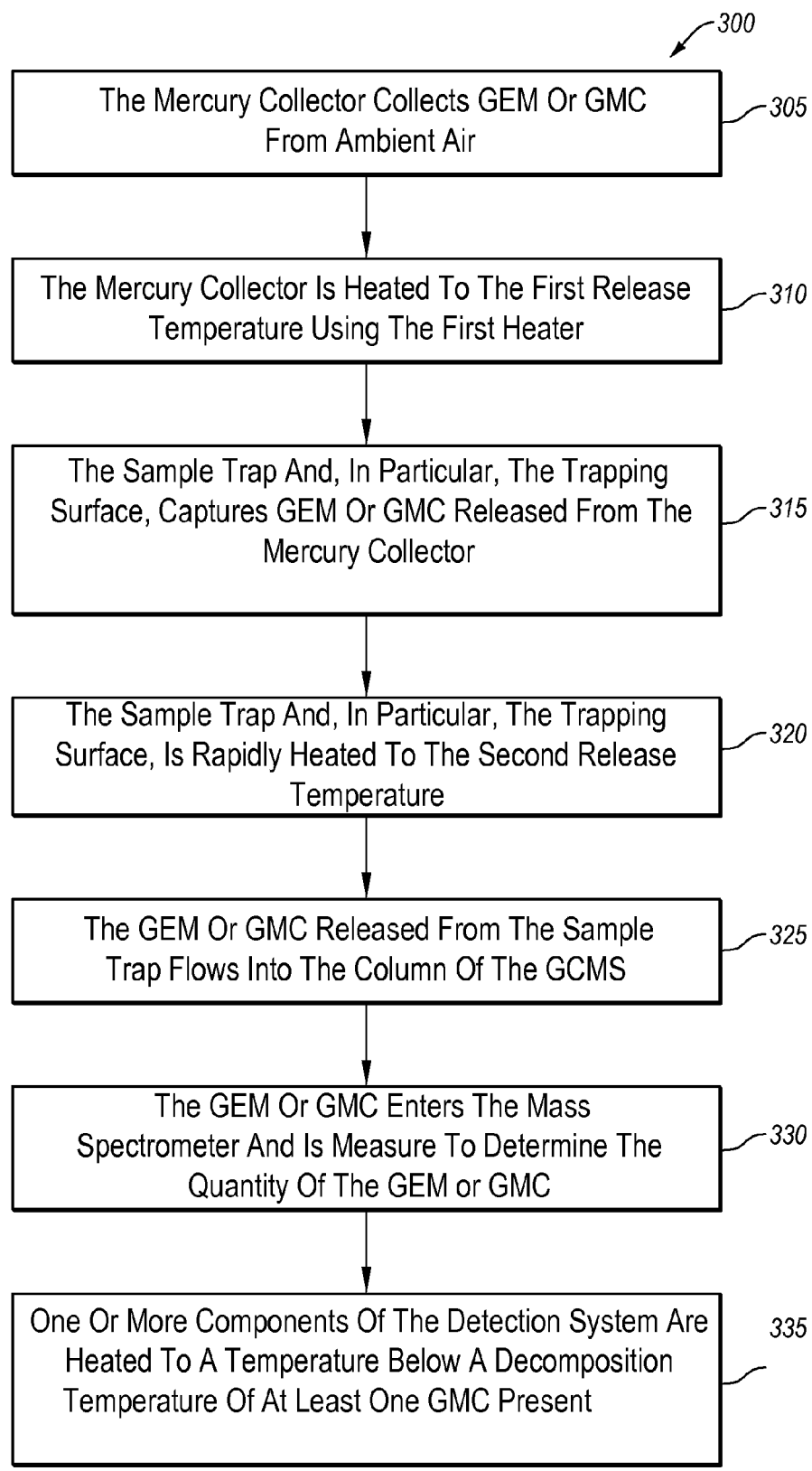
FIG. 3 is a flow diagram of a method of using the gaseous mercury detection system shown in FIGS. 2A and 2B, according to an embodiment.

FIG. 3 is a flow diagram of a method 300 of using the gaseous mercury detection system 200 shown in FIGS. 2A and 2B, according to an embodiment. In some embodiments, some of the acts of the method 300 may be split into a plurality of acts, some of the acts may be combined into a single act, and some acts may be omitted. Also, additional acts may be added to the method 300.

In act 305, the mercury collector 202 collects GEM or GMC from ambient air. In act 310, the mercury collector 202 is heated to the first release temperature using the first heater 206. The mercury collector 202 may be heated after the collection surface 203 has had sufficient time to collect the GEM or GMC from the ambient air, i.e., a sufficient amount of GEM or GMC to be accurately measured by the GCMS 204 after the GEM or GMC is or are concentrated by the sample trap 210.

In act 315, the sample trap 210 and, in particular the trapping surface 231, captures GEM or GMC released from the mercury collector 202. For example, the trapping surface 231 of the sample trap 210 may be cooled to a condensation temperature that is less than about 0° C.

In act 320, the sample trap 210, and in particular the trapping surface 231, may be rapidly heated to the second release temperature. The sample trap 210 may be heated to the second release temperature in about 2 seconds to about 2 minutes. Rapidly heating the sample trap 210 may cause the GEM or GMC to exit the sample trap 210 in higher concentrations than when the GEM or GMC exited the mercury collector 202. The higher concentrations of GEM or GMC may enable the GCMS 204 to measure the collected GEM or GMC.

In act 325, the GEM or GMC released from the sample trap 210 flows into the column 212 of the GCMS 204. The stationary phase of the column 212 may interact with the gases flowing therethrough to separate the GEM or GMC from other gases that flow through the column 212. Additionally, in some embodiments, the column 212 may interact with the GEM or GMC to separate individual constituents of the GEM or GMC from each other. For example, the column 212 may separate the GEM or each GMC from each other.

In act 330, the GEM or GMC that has passed through the column 212 enters the mass spectrometer 214 and may be measured to determine the quantity of the captured GEM or GMC. In some embodiments, prior to being measured, the GEM or GMC may be ionized by the ionizer 244. The ionizer 244 may include an electron ionizer, a chemical ionizer, or any suitable ionizer as previously described. The GCMS 204 may ionize and measure the GEM or GMC in response to direction from the controller 246.

In optional act 335, one or more components of the gaseous mercury detection system 200 may be heated to a temperature below a decomposition temperature of at least one GMC captured from the ambient air. The temperature may be selected to prevent at least one GEM or GMC from sticking to a surface of gaseous mercury detection system 200. For example, at least one of the second conduit 226 or the third conduit 242 may be heated to a temperature of about 100° C. to about 300° C.

Figure 4:
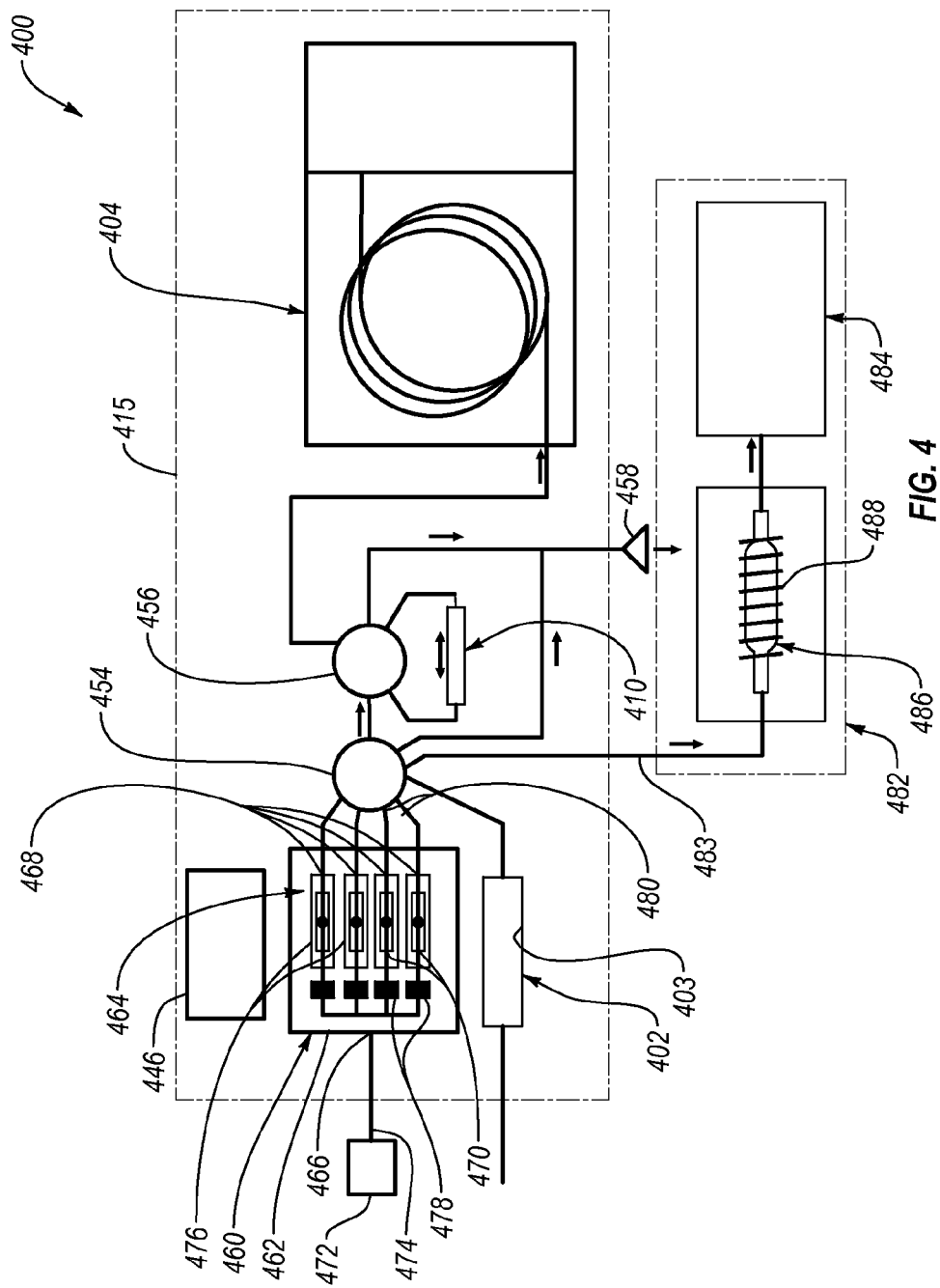
FIG. 4 is a schematic diagram of a gaseous mercury detection system configured to accurately measure GEM or GMC in ambient air and including at least part of an integrated calibration system, according to an embodiment.

FIG. 4 is a schematic diagram of a gaseous mercury detection system 400 configured to accurately detect GEM or GMC in ambient air and includes at least part of an integrated calibration system, according to an embodiment. In particular, the gaseous mercury detection system 400 may include a plurality of components configured to measure a quantity of GEM or GMC in ambient air, and a plurality of additional components (e.g., a permeation oven) configured to determine an accuracy of or calibrate the gaseous mercury detection system 400.

The gaseous mercury detection system 400 may include one or more components that are substantially similar to the components shown in FIGS. 2A and 2B, e.g., a support structure 415 and a mercury collector 402 with a collection surface 403 configured to collect GEM or GMC from the ambient air. The mercury collector 402 and, in particular, the collection surface 403 may be configured to release the GEM or GMC when the mercury collector 402 is heated to a first release temperature. The gaseous mercury detection system 400 may also include a sample trap 410 that is configured to release GEM or GMC in a concentration that can be accurately measured by the GCMS 404. For example, the sample trap 410 includes at least one trapping surface 431 configured to capture GEM or GMC released by the mercury collector 402. The sample trap 410 may then be rapidly heated to a second release temperature to release the GEM or GMC therefrom. The GEM or GMC may then flow into a GCMS 404 that measures the quantity of GEM or GMC present in the ambient air.

The gaseous mercury detection system 400 may include one or more valves configured to fluidly couple the components of the gaseous mercury detection system 400 to each other and controllably direct the flow of the GEM or GMC to the different components. For example, in the illustrated embodiment, the gaseous mercury detection system 400 includes a first valve 454 and a second valve 456. The first valve 454 may fluidly couple the mercury collector 402 to the second valve 456. The second valve 456 may fluidly couple the first valve 454, the sample trap 410, and the GCMS 404 to each other. The first valve 454 and the second valve 456 may be also fluidly couple one or more components of the detection system to a vent 458. The first valve 454 and the second valve 456 may be any suitable valve, such as a multi-port valve, an electrically activated valve, or combinations thereof. In some embodiment, at least one of the first valve 454 or the second valve 456 may direct the flow of the at least one mercury-containing gas in response to direction from the controller 444, from manual operation by a user of the gaseous mercury detection system 400, or any suitable method. In some embodiments, additional valves (e.g., a third valve) may be added to the gaseous mercury detection system 400. In other embodiments, the first valve 454 and the second valve 456 may be combined into a single valve. In other embodiments, the first valve 454 and the second valve 456 may be omitted.

The gaseous mercury detection system 400 further includes a permeation oven 460 that functions as part of a calibration system and is configured to determine an accuracy of or calibrate the gaseous mercury detection system 400. For example, the permeation oven 460 is configured to supply a known quantity of GEM or GMC. The known quantity of GEM or GMC may then be measured by the gaseous mercury detection system 400 to measure the quantity of GEM or GMC in ambient air. The known quantity of GEM or GMC supplied by the permeation oven 460 may be compared to the quantity of GEM or GMC measured by the gaseous mercury detection system 400 to determine the accuracy or calibrate the gaseous mercury detection system 400.

The permeation oven 460 may include at least one oven wall 462 that defines an internal heating chamber 464. The oven wall 462 may define at least one oven inlet 466 and at least one oven outlet 468 spaced from the oven inlet 466. The permeation oven 460 may be configured to have a fluid flow from the oven inlet 466 to the oven outlet 468. The permeation oven 460 may further include a filament or other heating device (not shown) positioned therein configured to heat the heating chamber 464 and contents therein to a selected temperature. The selected temperature may be any temperature below the decomposition temperature of at least one GMC supplied by the permeation oven 460. For example, the selected temperature may less than about 300° C., less than about 200° C., or about 100° C. The filament or other heating device may be configured to heat the heating chamber 464 to a selected temperature in response to direction from the controller 446.

The permeation oven 460 may also include one or more permeation tubes 470 positioned in the heating chamber 464. The permeation tubes 470 may include a compartment therein including elemental mercury or a mercury compound positioned therein. At least a portion of the permeation tubes 470 that defines the compartment may include a material that is semi-permeable to a vapor or gas of GEM or GMC (e.g., a permeable membrane), such as polyfluoroalkoxy alkane Teflon® heat shrinking tubing. At the selected temperature, the elemental mercury or mercury compound present in the compartment may evaporate or otherwise form GEM or a GMC. The GEM or GMC may be emitted from the permeation tubes 470. At a constant temperature, the emission rate of GEM or GMC may be substantially constant. The emission rate of the GEM or GMC at the selected temperature may be known (e.g., previously known or calculated by comparing the weight of the permeation tube 470 before and after the permeation tube 470 is heated).

In an embodiment, the permeation oven 460 may be configured to have a gas flow through the heating chamber 464 that is non-reactive with GEM or GMC. For example, the permeation oven 460 may be fluidly coupled to a gas supply 472 via at least one fourth conduit 474. The gas supply 472 may include, for example, a pressurized cylinder or a pump. The fourth conduit 474 may flow the gas from the gas supply 472 into the heating chamber 464 via the oven inlet 466.

In an embodiment, the permeation oven 460 may include one or more containers 476 positioned in the heating chamber 464 configured to support the one or more permeation tubes 470. Each container 476 may be positioned and configured such that a gas flowing through the heating chamber 464 flows around one or more individual permeation tubes 470 or around all permeation tubes 470 positioned on the containers 476. Additionally, the containers 476 may be configured to expose each permeation tube 470 to the selected temperature or to different, known temperatures, e.g., each permeation tube 470 may be heated to a different temperature.

In an embodiment, the containers 476 are configured to expose each permeation tube 470 positioned thereon to the heating chamber 464. For example, the container 476 may include a generally plate-like structure. In an embodiment, the containers 476 are configured to substantially seal the permeation tubes 470 from the heating chamber 464. For example, the containers 476 may include a generally conduit-like structure that is coupled to the oven inlet 466 via a conduit (e.g., the fourth conduit 474) and the oven outlet 468 via a conduit (e.g., the fifth conduit 480).

The permeation oven 460 is configured to flow a gas around each permeation tube 470 at a selected flow rate. For example, the fourth conduit 474 may be fluidly coupled to one or more orifices 478. Each of the orifices 478 may selectively control the rate at which the gas from the fourth conduit 474 flows therethrough. Each of the orifices 478 may also be fluidly coupled to one or more containers 476 that substantially seal each permeation tube therein from the rest of the heating chamber 464. As such, each permeation tube 470 may be exposed to a selected flow rate of the gas. The orifices 478 may operate in response to direction from the controller 446.

The permeation oven 460 may be fluidly coupled to one or more components of the gaseous mercury detection system 400. For example, in the illustrated embodiment, the permeation oven 460 may be fluidly coupled to the first valve 454 via at least one fifth conduit 480. The permeation oven 460 may then be fluidly coupled to at least one of the sample trap 410 or the GCMS 404 via the second valve 456. For example, the second valve 456 may direct the GEM or GMC supplied by the permeation oven 460 directly to the GCMS 404. Alternatively, the second valve 456 may direct the GEM or GMC to the sample trap 410 to be concentrated before directing the GEM or GMC to the GCMS 404. In an embodiment, the GEM or GMC supplied by the permeation oven 460 may first be directed to the mercury collector 402 before being directed to the sample trap 410 or the GCMS 404.

The GCMS 404 may measure the quantity of GEM or GMC supplied by the permeation oven 460. The gaseous mercury detection system 400 may then compare the quantity of GEM or GMC measured by the GCMS 404 to the known quantity of GEM or GMC supplied by the permeation oven 460. In some embodiments, the gaseous mercury detection system 400 may use the comparison to determine the accuracy of or calibrate the gaseous mercury detection system 400. In other embodiments, the gaseous mercury detection system 400 may be used to determine the known quantity of GEM or GMC supplied by the permeation oven 460.

The gaseous mercury detection system 400 may be fluidly coupled to a second mercury detection system 482 that is used to further determine the accuracy or calibrate the gaseous mercury detection system 400. In some embodiments, the second detection system 482 may be incorporated in the gaseous mercury detection system 400. For example, the second detection system 482 may be supported by the support structure 415. In other embodiments, the second detection system 482 may be distinct from the gaseous mercury detection system 400. For example, the second detection system 482 may be remote from the gaseous mercury detection system 400 and fluidly coupled to the gaseous mercury detection system 400 via at least one sixth conduit 483.

In an embodiment, the first valve 454 may selectively direct GEM or GMC collected to the second detection system 482. The GEM or GMC may be collected by the mercury collector 402 from ambient air or supplied by the permeation oven 460. The first valve 454 may direct the GEM or GMC to the second detection system 482 in response to direction from the controller 446. The second detection system 482 may then measure a quantity GEM or GMC provided thereto.

The second detection system 482 may include any gaseous mercury detection system. In an embodiment, the second detection system 482 may be substantially similar to the gaseous mercury detection system 200 shown in FIGS. 2A and 2B that has been previously calibrated. In the illustrated embodiment, the second detection system 482 may include an elemental mercury detector 484 (EMD). The EMD 484 may include any EMD known in the art. For example, the EMD 484 may include a Tekran® 2537. In an embodiment, the EMD 484 may include a Tekran® 1130 coupled to a Tekran® 1135 and a Tekran® 2537.

The second detection system 482 may further include a pyrolyzer 486 positioned between the EMD 484 and the first valve 454 configured to collect the GEM or GMC. In an embodiment, the pyrolyzer 486 may be similar to the mercury collector 102 shown in FIG. 1. For example, the pyrolyzer 486 may include a pyrolyzer collection surface 490 configured to collect GEM or GMC. The pyrolyzer collection surface 490 may include a potassium chloride collection surface. The pyrolyzer 486 and, in particular, the pyrolyzer collection surface 490, may release the GEM or GMC when the pyrolyzer 486 is heated above the decomposition temperature of at least one GMC that may be present. The second detection system 482 may include a heater 488 configured to heat the pyrolyzer 486 above the decomposition temperature of the at least one GMC.

In an embodiment, one or more components of the gaseous mercury detection system 400 and the second detection system 482 may be heated to a temperature between about 100° C. to about 300° C. (e.g., about 150° C. to about 250° C., about 200° C.) when a mercury-containing gas flows therethrough. The one or more components of the gaseous mercury detection system 400 and second detection system 482 may be heated to minimize (e.g., substantially prevent) the amount of GEM or GMC adhering to a surface of the one or more components. For example, the first valve 454, the second valve 456, the fourth conduit 474, the fifth conduit 480, the sixth conduit 483, the GCMS 404, or another component of the gaseous mercury detection system 400 may be heated to a temperature between about 100° C. to about 300° C. (e.g., 150° C. to about 250° C., about 200° C.) when the GEM or GMC flow therethrough. Additionally or alternatively, the one or more components of the gaseous mercury detection system 400 and the second detection system 482 (e.g., the containers 672, the first valve 454, the fourth conduit 474, etc.) may include a substantially nonpolar coating applied to an interior surface thereof that contacts the GEM or GMC to minimize the amount of GEM or GMC that sticks thereto. The nonpolar coating may include, for example, deactivated fused silica, PDMS, or combinations thereof.

Figure 5:
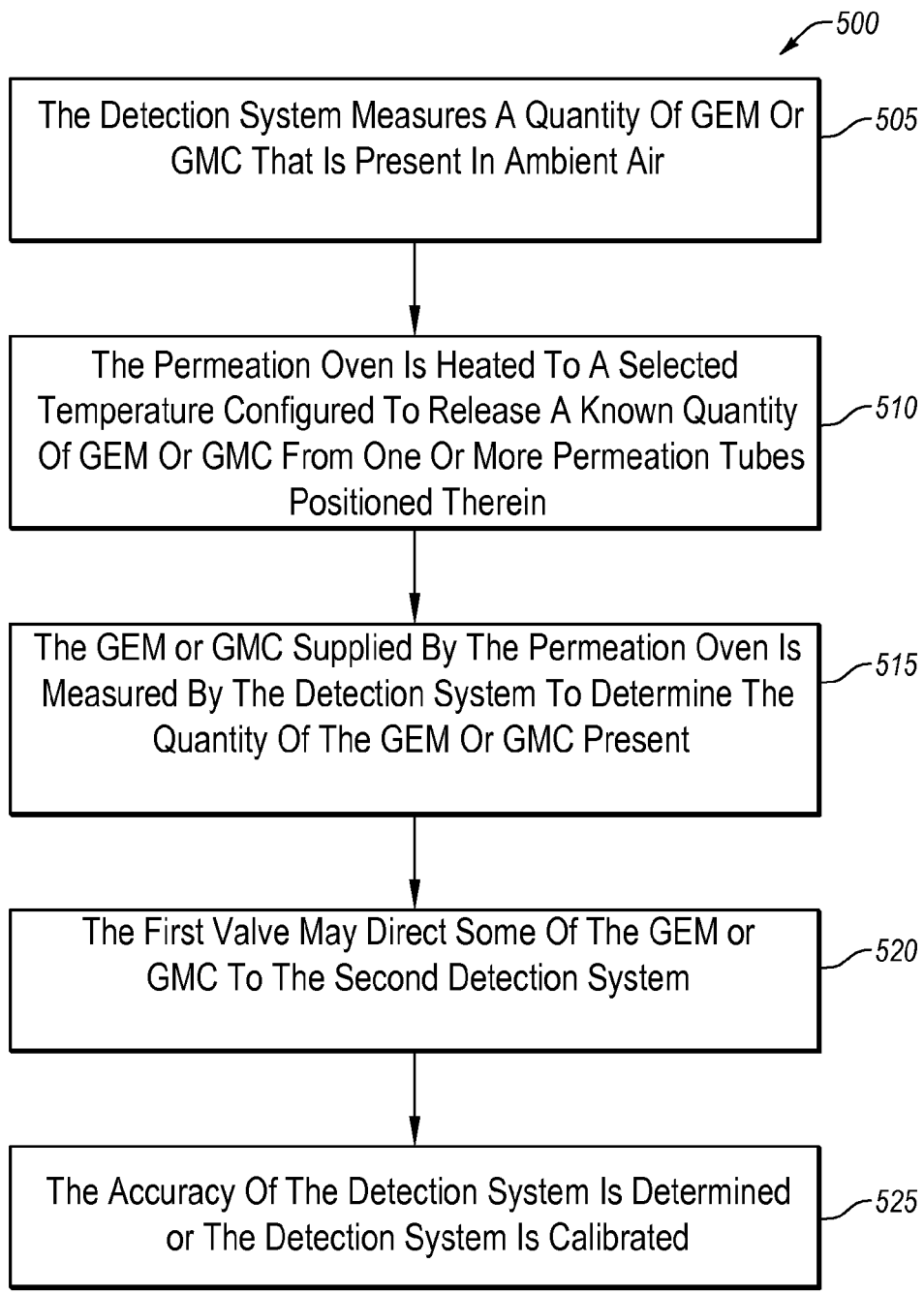
FIG. 5 is a flow diagram of a method of using the gaseous mercury detection system shown in FIG. 4, according to an embodiment.

FIG. 5 is a flow diagram of a method 500 of using the gaseous mercury detection system 400 shown in FIG. 4, according to an embodiment. In some embodiments, some of the acts of the method 500 may be split into a plurality of acts, some of the acts may be combined into a single act, and some acts may be omitted. Also, additional acts may be added to the method 500.

In act 505, the gaseous mercury detection system 400 measures a quantity of GEM or GMC that is present in ambient air. For example, the mercury collector 402 may collect the GEM or GMC from ambient air that flows therethrough. The mercury collector 402 and, in particular, the collection surface 403 of the mercury collector 402, may release the GEM or GMC when the mercury collector 402 is heated to the first release temperature. The GEM or GMC may then be captured by the sample trap 410 that is fluidly coupled to the mercury collector 402. The sample trap 410 may release the GEM or GMC when heated to a second release temperature. The GEM or GMC exiting the sample trap 410 may exhibit a higher concentration than the GEM or GMC exiting the mercury collector 402. The GCMS 404 may measure the quantity of GEM or GMC present therein. In an embodiment, these steps may be in response to direction from the controller 446, or combinations thereof.

In act 510, the permeation oven 460 is heated to a selected temperature configured to release a known quantity of GEM or GMC from one or more permeation tubes 470 positioned therein. For example, the one or more permeation tubes 470 may include at least one of elemental mercury or at least one mercury compound therein. When the one or more permeation tubes 470 are heated to the selected temperature, the elemental mercury or the mercury compound may form at least one of GEM or GMC. The GEM or the GMC may be emitted from the permeation tubes 470 at a known emission rate. In an embodiment, the emission rate of the permeation tubes 470 at the selected temperature may be known prior to performing act 510 or may be determined after act 510. In an embodiment, a gas that is non-reactive with GEM or GMC emitted by the permeation tubes 470 may flow through the permeation oven 460 to move the GEM or GMC towards the oven outlet 468. It should be noted that act 510 may be performed before or after act 505. The permeation oven 460 may be heated in response to direction from the controller 446.

In act 515, the GEM or GMC supplied by the permeation oven 460 are measured by the gaseous mercury detection system 400 to determine the quantity of GEM or GMC present. For example, the GEM or GMC may flow from the permeation oven 460 to the first valve 454 and from the first valve 454 to the second valve 456. In some embodiments, the second valve 456 may direct the GEM or GMC to the sample trap 410. The sample trap 410 may capture the GEM or GMC and then rapidly heat to release the GEM or GMC. The GEM or GMC exiting the sample trap 410 may exhibit a higher concentration than the GEM or GMC exiting the permeation oven 460. The second valve 456 may direct the GEM or GMC to the GCMS 404. The GCMS 404 may measure the quantity of GEM or GMC supplied by the permeation oven 460.

In act 520, the first valve 454 may direct some of the GEM or GMC to the second detection system 482. The GEM or GMC may first flow through the pyrolyzer 486 that collects the GEM or GMC and release GEM when heated above a decomposition temperature of at least one GMC present. The GEM may then be analyzed by the EMD 484 to determine the quantity of elemental mercury contained therein after the GMC is decomposed (e.g., GEM and elemental mercury from the decomposed GMC). The GEM or GMC may be directed towards the second detection system 482 and the second detection system 482 may measure the GEM or GMC in response to direction from the controller 446.

In act 525, the accuracy of the gaseous mercury detection system 400 is determined or the detection system is calibrated. For example, the quantity of the GEM or GMC collected by the mercury collector 402 from ambient air detected by the GCMS 404 may be compared to the quantity of GEM or GMC collected by the mercury collector 402 from ambient air detected by the second detection system 482. In an embodiment, the known quantity of GEM or GMC supplied by the permeation oven 460 is compared to the quantity of GEM or GMC supplied by the permeation oven 460 that is measured by the GCMS 404. In an embodiment, the quantity of GEM or GMC supplied by the permeation oven 460 that is measured by the GCMS 404 is compared to the quantity of GEM or GMC supplied by the permeation oven 460 that is measured by the second detection system 482. Alternatively, the gaseous mercury detection system 400 may use one or more of the above comparisons to determine the accuracy of or calibrate the gaseous mercury detection system 400. For example, the gaseous mercury detection system 400 may use the comparison to determine a correction factor that may compensate for any discrepancies between the two quantities.

The following working example provides further detail in connection with the specific embodiments described above.

Working Example

A gaseous mercury detection system was provided that was similar to the gaseous mercury detection system 400 shown in FIG. 4. The gaseous mercury detection system detection system included a gas supply having a high purity helium source and a permeation oven fluidly coupled to the gas supply. The permeation oven included a container therein. The container included a one-quarter inch stainless steel tube that was coated with SilcoNert® deactivated fused silica. A permeation tube was placed inside the container. The permeation tube included a one-eighth inch diameter polyfluoroalkoxy alkane heat-shrink tubing with polytetrafluoroethylene plugs that sealed both ends of the permeation tube. Mercury bromide (HgBr$_2$) was placed within the permeation tube between the polytetrafluoroethylene plugs.

The gaseous mercury detection system also included a sample trap. The sample trap was an SIS Model 961 cryogenic focusing unit. The sample trap included a 0.25 millimeter inner-diameter deactivated fused silica tube. The gaseous mercury detection system included a first conduit that fluidly coupled the permeation oven on to the sample trap. The first conduit included stainless steel tubing that had an inner surface thereof coated with SilcoNert® deactivated fused silica. The first conduit also included two stainless steel VICI GC valves that had an inner surface coated with SilcoNert® deactivated fused silica.

The gaseous mercury detection system also included a Shimadzu QP2010 Ultra GCMS. The GCMS included a column and a mass spectrometer. The column included a 30-meter long tubing that had a 0.25 mm inner diameter. The inner surface of the tubing was coated with PDMS. The mass spectrometer included an electron ionizer. Finally, the gaseous mercury detection system included a second conduit that fluidly coupled the sample trap to the GCMS. The second conduit included stainless steel tubing that had an inner surface thereof coated with SilcoNert® deactivated fused silica.

During operation, the permeation tube was heated to about 100° C. to form a mercury-containing gas. A 30 millimeter per minute flow of high purity helium gas was flowed through the container to transport the mercury-containing gas emitted from the permeation tube to the sample trap. The mercury-containing gas flowed from the permeation oven to the sample trap via the first conduit which was heated to about 220° C. The trapping surface of the sample trap was cooled to about 0° C. to capture the mercury-containing gas. The trapping surface was allowed to capture the mercury-containing gas for about 5 minutes after which the trapping surface was rapidly heated to about 220° C. The trapping surface was held at about 220° C. for about 10 minutes (e.g., the time it took the GCMS to measure the at least one mercury-containing gas). The mercury-containing gas flowed from the sample trap to the GCMS via the second conduit, which was heated to about 200° C. The quantity of the mercury-containing gas was then measured by the GCMS.

Figure 6A:
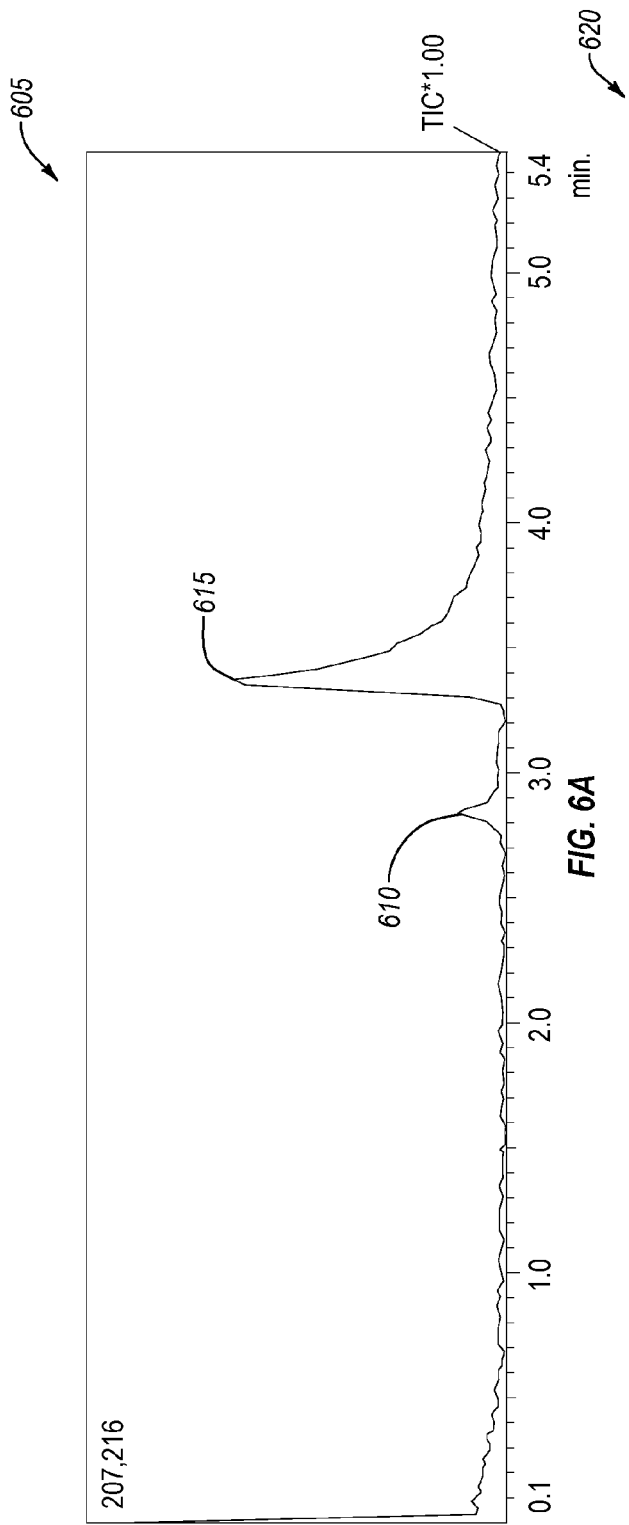
FIGS. 6A and 6B are graphs outputted by a GCMS after the GCMS measured a quantity of different mercury-containing gases.
Figure 6B:
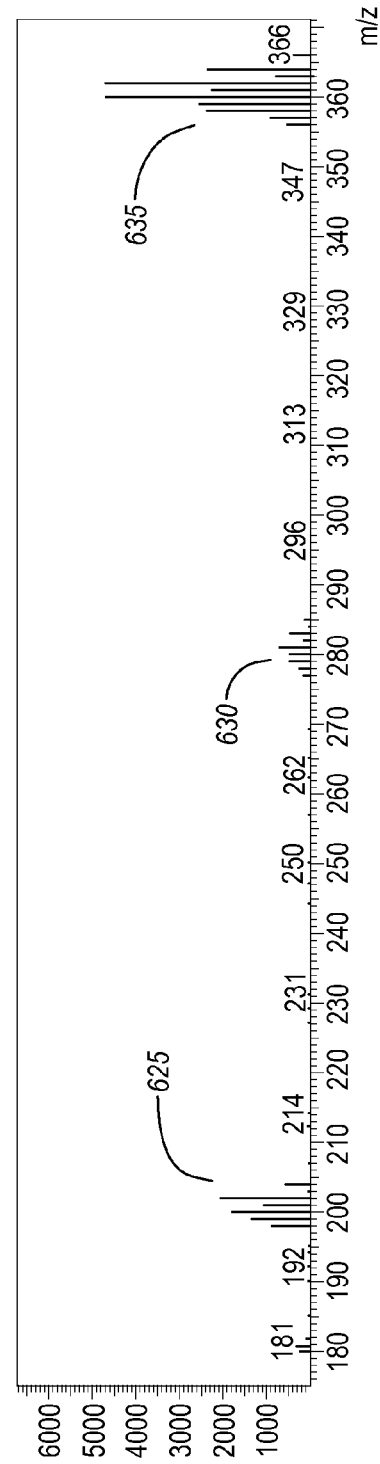

FIGS. 6A and 6B are graphs outputted by the GCMS after the GCMS measured the quantity of the mercury-containing gas. FIG. 6A is a chromatogram 605 that plots relative intensity (e.g., abundance) of the mercury-containing gas measured by the GCMS as a function of time. The chromatogram 605 includes first peak 610 at about 2.8 minutes corresponding to GEM and a second peak 615 at about 3.4 minutes corresponding to mercury bromide. The chromatogram 605 illustrates that the gaseous mercury detection system can measure both GEM and GMC. FIG. 6B is a mass spectrum 620 of the mercury-containing gas detected by the GCMS at about 3.4 minutes. The mass spectrum 620 plots the relative intensity of the gas detected at about 3.4 minutes as a function of its mass to charge ratio (m/z). The mass spectrum 620 includes a first peak 625 that corresponds to GEM ($^{202}$Hg,) a second peak 630 that corresponds to HgBr ($^{202}$Hg+$^{79}$Br), and a third peak 635 that corresponds to HgBr$_2$ ($^{202}$Hg+$^{79}$Br+$^{81}$Br). At least some of the GEM shown in the chromatogram 605 may be caused by decomposition of the mercury bromide caused by the electron ionizer. Using the information shown in FIGS. 6A and 6B, the detection system may determine the quantity of GEM and GMC present in the mercury-containing gas.

Figure 7:
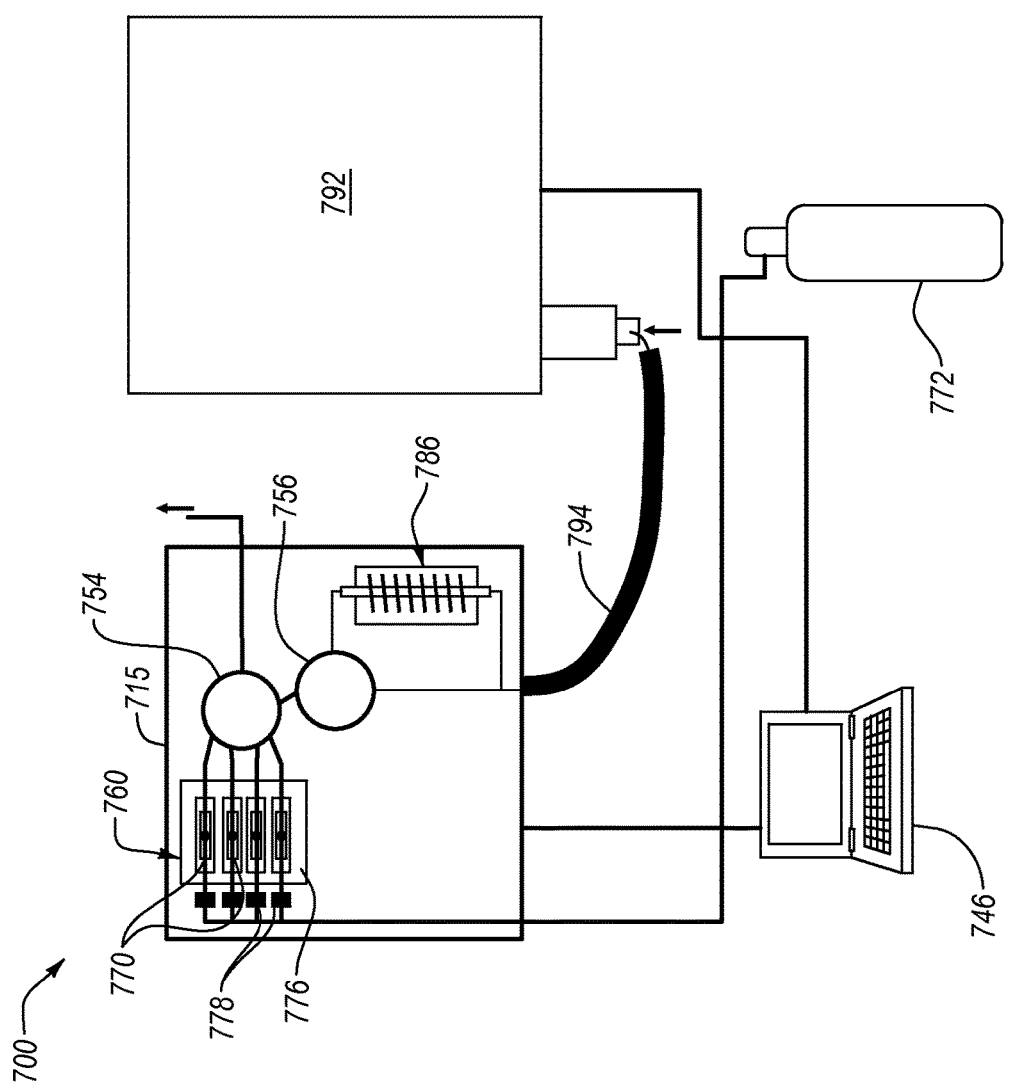
FIG. 7 is a schematic illustration of a calibration system that may be used to calibrate any gaseous mercury detection system disclosed herein or conventional gaseous mercury detection systems, according to an embodiment.

FIG. 7 is a schematic diagram of a calibration system 700, according to an embodiment. The calibration system 700 may be used to calibrate any gaseous mercury detection system disclosed herein or any conventional gaseous mercury detection system. The calibration system 700 is configured to supply a known quantity of mercury-containing gas to a gaseous mercury detector 792. The gaseous mercury detector 792 may detect a quantity of GEM or GMC. The calibration system 700 may also include a controller 746 that is communicably coupled to the calibration system 700 and the gaseous mercury detector 792. The controller 746 may be configured to compare the quantity of the GEM or GMC detected by the gaseous mercury detector 792 to the known quantity of the GEM or GMC provided by the calibration system 700. As such, the controller 746 may at least one of determine an accuracy of or calibrate the gaseous mercury detector 792.

The calibration system 700 may include a support structure 715.

The calibration system 700 further includes a permeation oven 760. The permeation oven 760 may be substantially similar to the permeation oven 460 shown in FIG. 4. For example, the permeation oven 760 may include one or more permeation tubes 770 positioned therein. The permeation oven 760 may also include a filament or other heating device (not shown) configured to heat the one or more permeation tubes 770 to a selected temperature. The one or more permeation tubes 770 may include elemental mercury or a mercury compound therein. The elemental mercury or the mercury compound partially vaporizes or otherwise forms GEM or GMC (e.g., at least one mercury-containing gas). The one or more permeation tubes 770 emit the mercury-containing gas at a known (e.g., already known or determinable) emission rate at the selected temperature. As such, the permeation tubes 770 may supply a known quantity of the mercury-containing gas.

In an embodiment, the permeation oven 760 may be fluidly coupled to a gas supply 772 that supplies the permeation oven 760 with a supply of a gas that is non-reactive with the mercury-containing gas (e.g., Argon, Helium, or another noble gas and/or another inert gas). The gas may transport the mercury-containing gas from the permeation oven 760. In some embodiments, the permeation oven 760 may be configured to flow a selected amount of the gas around each permeation tube 770. For example, at least one permeation tube 770 may be placed in container 776 that is connected to an orifice 778. The orifice 778 may be configured to only allow a selected amount, rate, or pressure of the gas to flow through the container 776.

The calibration system 700 may further include one or more valves configured to direct the mercury-containing gas that exits the permeation oven 760 to other components of the calibration system 700. For example, the one or more valves may include a first valve 754 and a second valve 756. The first valve 754 may fluidly couple the permeation oven 760 (e.g., fluidly coupled to each container 776) to the second valve 756. The second valve 756 may be configured to direct the at least one mercury-containing gas to one or more different components of the calibration system 700. For example, the second valve 756 may be fluidly coupled to a pyrolyzer 786. In an embodiment, the second valve 756 may direct the mercury-containing gas to a mercury collector (not shown) or sample trap (not shown). The pyrolyzer 786, the mercury collector, or the sample trap may release the mercury-containing gas when heated above their respective release temperatures. The calibration system 700 may include a conduit 794 that fluidly couples the pyrolyzer 786, the mercury collector, or the sample trap to the gaseous mercury detector 792. In another example, the second valve 756 may also be fluidly coupled to the conduit 794.

In an embodiment, the first valve 754, the second valve 756, conduit 794, or another component of the calibration system 700 may be heated to a temperature between about 100° C. to about 300° C., such as about 150° C. to about 250° C. or about 220° C. to minimize (e.g., substantially prevent) the at least one mercury-containing gas from sticking to the surfaces thereof. Additionally or alternatively, the first valve 754, the second valve 756, conduit 794, or another component of the calibration system 700 that comes in contact with the mercury-containing gas may be coated with a substantially nonpolar coating, such as a deactivated fused silica coating (e.g., SilcoNert® deactivated fused silica) and/or a PDMS coating. The coating may help minimize (e.g., substantially prevent) the mercury-containing gas from adhering to the components of the calibration system 700.

The conduit 794 fluidly couples the calibration system 700 to the gaseous mercury detector 792. The gaseous mercury detector 792 may receive the known quantity of the mercury-containing gas and detect the quantity of the mercury-containing gas. The gaseous mercury detector 792 may be substantially similar to the gaseous mercury detection system 200 shown in FIGS. 2A and 2B or the second detection system 482 shown in FIG. 4.

The controller 746 may be communicably coupled to one or more components of the calibration system 700 and the gaseous mercury detector 792. In an embodiment, the controller 746 may control the one or more components of the calibration system 700 and the gaseous mercury detector 792. In an embodiment, the controller 746 may compare the quantity of the at least one mercury-containing gas detected by the gaseous mercury detector 792 with the known quantity of the at least one mercury-containing gas supplied by the calibration system 700. The controller 746 may use this comparison to determine the accuracy of the gaseous mercury detector 792 and calibrate the gaseous mercury detector 792 using any of the calibration techniques previously discussed.

Embodiments of the present disclosure may be embodied in other specific forms without departing from its spirit or essential characteristics. The described embodiments are to be considered in all respects only as illustrative, and not restrictive. All changes which come within the meaning and range of equivalency of the foregoing description are to be embraced within the scope of the invention.

What is claimed is:

1. A method of collecting and releasing gaseous elemental mercury (GEM), Gaseous Mercury Bromide, or Gaseous Mercury Chloride, in ambient air, the method comprising:
    cooling a collection surface to a collection temperature within five degrees Celsius above the ambient air dew point temperature;
    drawing over the collection surface the ambient air at a collection flow rate;
    collecting on the collection surface the at least one of GEM, Gaseous Mercury Bromide, or Gaseous Mercury Chloride present in the ambient air, the GEM, Gaseous Mercury Bromide, and Gaseous Mercury Chloride becoming Elemental Mercury, Mercury Bromide, and Mercury Chloride on the collection surface;
    heating the collection surface to a temperature sufficient to release the at least one of Elemental Mercury, Mercury Bromide, or Mercury Chloride therefrom and below the lowest of the decomposition temperatures of Mercury Bromide and Mercury Chloride; and
    releasing from the collection surface the at least one of the Elemental Mercury, Mercury Bromide, or Mercury Chloride collected thereon, the Elemental Mercury, Mercury Bromide, or Mercury Chloride becoming GEM, Gaseous Mercury Bromide, and Gaseous Mercury Chloride, respectively.

2. A method of measuring a quantity of gaseous elemental mercury (GEM), Gaseous Mercury Bromide, or Gaseous Mercury Chloride, in ambient air, the method comprising:
    cooling a collection surface to a collection temperature within five degrees Celsius above the ambient air dew point temperature;
    drawing over the collection surface the ambient air at a collection flow rate;
    collecting on the collection surface the at least one of GEM, Gaseous Mercury Bromide, or Gaseous Mercury Chloride present in the ambient air, the GEM, Gaseous Mercury Bromide, and Gaseous Mercury Chloride becoming Elemental Mercury, Mercury Bromide, and Mercury Chloride, respectively, on the collection surface;
    passing over the collection surface a gas that is non-reactive with Elemental Mercury, Mercury Bromide, or Mercury Chloride and heating the collection surface to a temperature sufficient to release the at least one of the Elemental Mercury, Mercury Bromide, or Mercury Chloride therefrom and below the lowest of the decomposition temperatures of Mercury Bromide and Mercury Chloride;
    releasing from the collection surface the at least one of the Elemental Mercury, Mercury Bromide, or Mercury Chloride collected thereon to form GEM, Gaseous Mercury Bromide, or Gaseous Mercury Chloride;
    cooling a sample trap to a temperature of about 0° C. or less;
    capturing the at least one of the GEM, Gaseous Mercury Bromide, or Gaseous Mercury Chloride released from the collection surface into the sample trap, the GEM, Gaseous Mercury Bromide, and Gaseous Mercury Chloride becoming Elemental Mercury, Mercury Bromide, and Mercury Chloride, respectively, in the sample trap;
    heating the sample trap to a temperature up to the lowest of the decomposition temperatures of Mercury Bromide or Mercury Chloride;
    desorbing the at least one of the Elemental Mercury, Mercury Bromide, or Mercury Chloride from the sample trap, the Elemental Mercury, Mercury Bromide, and Mercury Chloride becoming GEM, Gaseous Mercury Bromide, and Gaseous Mercury, respectively, in a mercury-containing gas; and
    after heating the sample trap, measuring at least one of a quantity of the GEM, Gaseous Mercury Bromide, or Gaseous Mercury Chloride in the mercury-containing gas using a gas-chromatography mass spectrometer.

3. The method of claim 2, wherein the collection flow rate is about 10 to about 100 liters per minute.

4. The method of claim 2, wherein the cooling the sample trap includes cooling the sample trap to a temperature of about −50° C.

5. The method of claim 2, wherein the collecting on the collection surface occurs over a period of 30 minutes to two hours.

6. The method of claim 2, further comprising, prior to measuring, ionizing the mercury-containing gas using an electron ionizer.

7. The method of claim 2, further comprising, prior to measuring, ionizing the mercury-containing gas using a chemical ionizer.

8. The method of claim 2, further comprising calibrating the gas-chromatography mass spectrometer, wherein calibrating the gas-chromatography mass spectrometer includes:
    heating a permeation oven to a selected temperature, the permeation oven including one or more permeation tubes therein having at least one of elemental mercury, Mercury Bromide, or Mercury Chloride and configured to release the at least one of the elemental mercury, Mercury Bromide, or Mercury Chloride stored therein at the selected temperature as GEM, Gaseous Mercury Bromide or Gaseous Mercury Chloride; and measuring the quantity of the at least one of the GEM, Gaseous Mercury Bromide or the Gaseous Mercury Chloride released by the one or more permeation tubes using the gas-chromatography mass spectrometer.

* * * * *